(12) United States Patent
Messina et al.

(10) Patent No.: US 10,208,300 B2
(45) Date of Patent: Feb. 19, 2019

(54) **EXTRACELLULAR HYALURONIDASE FROM *STREPTOMYCES KOGANEIENSIS***

(71) Applicant: FIDIA FARMACEUTICI S.P.A., Abano Terme Pd (IT)

(72) Inventors: Luciano Messina, Abano Terme (IT); Susanna Vaccaro, Abano Terme Pd (IT); Salvatore Caruso, Abano Terme Pd (IT); Giovanni Gennari, Abano Terme (IT)

(73) Assignee: FIDIA FARMACEUTICI S.P.A., Abano Terme (PD) (IT)

( * ) Notice: Subject to any disclaimer, the term of this patent is extended or adjusted under 35 U.S.C. 154(b) by 0 days.

(21) Appl. No.: 15/226,593

(22) Filed: Aug. 2, 2016

(65) Prior Publication Data

US 2017/0101634 A1    Apr. 13, 2017

Related U.S. Application Data

(62) Division of application No. 13/318,476, filed as application No. PCT/EP2010/056596 on May 12, 2010, now abandoned.

(30) Foreign Application Priority Data

May 14, 2009 (IT) .............. MI2009A0831

(51) Int. Cl.
| | |
|---|---|
| *C12N 13/00* | (2006.01) |
| *C12N 9/26* | (2006.01) |
| *C07K 14/315* | (2006.01) |
| *C07K 14/435* | (2006.01) |
| *A61K 38/47* | (2006.01) |
| *A61K 39/35* | (2006.01) |
| *A61K 45/06* | (2006.01) |
| *A61K 38/00* | (2006.01) |

(52) U.S. Cl.
CPC ............ *C12N 9/2474* (2013.01); *A61K 38/47* (2013.01); *A61K 39/35* (2013.01); *A61K 45/06* (2013.01); *C07K 14/315* (2013.01); *C07K 14/43595* (2013.01); *C12N 9/2408* (2013.01); *C12Y 302/01035* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 4,258,134 | A * | 3/1981 | Yoshida | C12N 9/2408 435/201 |
| 7,345,117 | B1 | 3/2008 | Barbucci et al. | |
| 2009/0197807 | A1 | 8/2009 | Callegaro et al. | |
| 2012/0070441 | A1* | 3/2012 | Messina | C12N 9/2408 424/141.1 |

FOREIGN PATENT DOCUMENTS

EP    0005751 A1    12/1979

* cited by examiner

*Primary Examiner* — Hope Robinson
(74) *Attorney, Agent, or Firm* — Birch, Stewart, Kolasch & Birch, LLP

(57) ABSTRACT

A process for preparing *Streptomyces koganeiensis* ATCC 31394 hyaluronidase by obtaining hyaluronidase having molecular weight of 21.6 kDalton, which has hyaluronidase activity and stability markedly higher than those of the hyaluronidase obtained from such microorganism to date.

1 Claim, 16 Drawing Sheets

Specification includes a Sequence Listing.

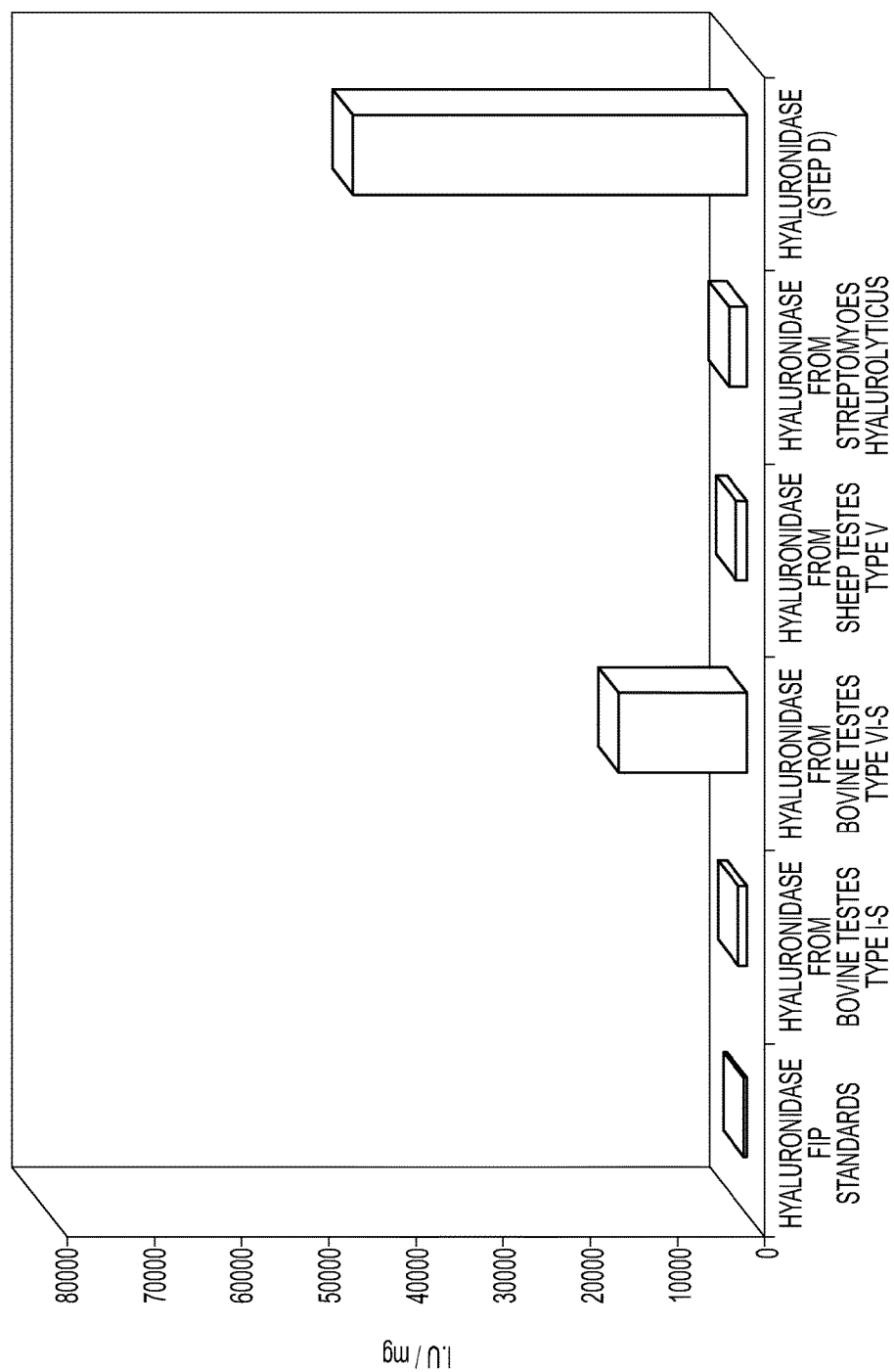

EXTRACELLULAR HYALURONIDASE FROM *STREPTOMYCES KOGANEIENSIS*

CROSS REFERENCE TO RELATED APPLICATIONS

This application is a Divisional Application of U.S. application Ser. No. 13/318,476 filed on Nov. 30, 2011, which is the National Phase of International Application No. PCT/EP2010/056596 which has an International filing date of May 12, 2010, which claims priority to Italian Application No. MI2009A000831 filed on May 14, 2009, all of which are hereby expressly incorporated by reference into the present application.

STATE OF THE TECHNIQUE

Hyaluronidase is a hydrolytic enzyme that cleaves hyaluronic acid to D-glucuronic acid and N-acetylglucosamine; in varying manner, it is also able to degrade other acid mucopolysaccharides of the connective tissue. For example, high concentrations of hyaluronidase are found, in the buccal apparatus of leeches, in the venoms of snakes, bees, scorpions and in the culture supernatants of pathogenic bacteria such as pneumococci, β-hemolytic streptococci and *Staphylococcus aureus*. In the human body hyaluronidase is found in the cornea, ciliary body, spleen, skin and testicles. High amounts of hyaluronidase are also found in spermatozoa, thus allowing them to cross the hyaluronic acid barrier that protects the egg cells.

Hyaluronidase is used in medicine in the treatment of edema, local inflammatory states, hemorrhoids and chilblains and to facilitate the subcutaneous administration of some active ingredients. Some hyaluronidases were also reported to be able to determine a significant reduction in the size of myocardial infarction [1]. In the veterinary field it is used in antibiotic solutions for the treatment of animal diseases, such as bovine mastitis. Furthermore, hyaluronidase can be used as an analytical reagent in some biological assays, for example in the quali-quantitative determination of hyaluronic acid.

The industrial-scale production and purification of bacterial or animal hyaluronidases are difficult due to the fact that the enzyme becomes unstable in aqueous solution and loses activity upon purification.

U.S. Pat. No. 4,258,134 and the corresponding European patent EP 0 005 751 [2] disclose a hyaluronidase obtained by dialysis and DEAE- and CM-cellulose ion exchange chromatography of the culture supernatant of *Streptomyces koganeiensis* ATCC 31394.

It has now been found that such protein fraction, obtained after the two chromatography steps, is indeed made of numerous protein components (about 68 in bidimensional electrophoresis), but only one of them has high hyaluronidase activity and marked stability.

DETAILED DESCRIPTION OF THE INVENTION

The invention relates to hyaluronidase from *Streptomyces koganeiensis* ATCC 31394 comprising the N-terminal amino acid sequence shown in SEQ ID NO: 1.

The enzyme is also characterized by molecular weight of 21.6 kDa, isoelectric point (pI) ranging between 4.4-4.8 and enzyme activity equal to or higher than 40,000 I.U./mg.

The hyaluronidase according to the invention can be obtained by a process including the following steps:

a) subjecting the supernatant obtained from fermentation of *Streptomyces koganeiensis* ATCC 31394 to weak cation-exchange chromatography and isolating the protein fraction with hyaluronidase activity;

b) subjecting the protein fraction with hyaluronidase activity obtained in step a) to diafiltration and strong anion-exchange chromatography and isolating the protein fraction with hyaluronidase activity;

c) subjecting the protein fraction with hyaluronidase activity obtained in step b) to strong cation-exchange chromatography and isolating the protein fraction with hyaluronidase activity;

d) subjecting the protein fraction with hyaluronidase activity obtained in step c) to strong anion-exchange chromatography and isolating the protein fraction with hyaluronidase activity.

Fermentation of the microorganism can be carried out by known methods, particularly the method disclosed in U.S. Pat. No. 4,258,134. The supernatant obtained upon fermentation is then collected, centrifuged and filtered. Furthermore, before being subjected to the chromatography steps according to the invention, the supernatant can be subjected to further treatments aimed at removing residual particulate from the culture, by methods and techniques known to the skilled person. Usually, the centrifuged and filtered supernatant is subjected to concentration and dialysis. Typically, concentration is carried out by ultrafiltration on appropriate polyethersulfone filters with cut-off ranging between 5 and 15 kDa, preferably of 10 kDa; usually the supernatant is concentrated 8 to 12 fold, preferably 10 fold. Once the presence of hyaluronidase activity is verified by a proper assay, for example the modified assay of Dorfman [3], the concentrated supernatant is dialysed with a buffer solution that is chosen depending on the weak cation-exchange resin used in step a), in such a way that hyaluronidase is at such pH conditions as to be able to bind to the resin; this resin comprises carboxyalkyl exchange groups, preferably carboxymethyl groups, such as the "CM-Sepharose® Fast Flow" resin. After properly equilibrating the resin with the same buffer solution in which dialysis was carried out, the sample is loaded and elution is then performed with the same solution to remove unbound proteins, after which the pH is increased to elute bound proteins. When the "CM-Sepharose® Fast Flow" resin is used, dialysis, resin equilibration and unbound proteins elution are carried out with 50 mM sodium acetate solution at pH 4.0, while bound proteins elution is carried out with 50 mM sodium acetate solution at pH 4.5. The bound proteins that exhibit high hyaluronidase activity are pooled in a single fraction and subjected to strong anion-exchange chromatography [step b)]. Before proceeding, the pooled fractions are clarified by diafiltration, which is carried out by means and methods known to the skilled person, using a buffer solution that allows hyaluronidase to bind to the strong anion-exchange resin used in step b). Such resin comprises trialkylammonium groups, typically trimethylammonium groups, such as the HiTrap® Q XL resin (5 ml column). After equilibrating the resin with the same solution used for diafiltration, the fraction obtained in step a) is loaded and elution is then performed with the same solution to remove unbound proteins; then the eluent ionic strength is progressively increased to elute bound proteins. According to a preferred embodiment, the HiTrap® Q XL resin is used and diafiltration, column equilibration and unbound proteins elution are carried out with 50 mM Tris-HCl buffer solution at pH 8, while bound proteins elution is carried out by adding NaCl at increasing concentrations to the eluent. By first eluting with 50 mM Tris-HCl, 35 mM NaCl solution at pH 8 and then 50 mM Tris-HCl, 200 mM NaCl solution at pH 8 two fractions are thus obtained, only the second of which, eluted with the solution containing 200 mM NaCl, exhibits hyaluronidase activity. Such fraction is diluted 8-12 fold, preferably 10 fold, with a buffer solution that allows hyaluronidase to bind to the strong cation-exchange resin used for step c). The resin comprises sulfonic groups, preferably sulfonyl alkyl groups, even more preferably sulfonyl propyl groups; according to a particularly preferred embodiment of the invention, the "HiTrap® SP FF" resin is used. Practically, after equilibrating the resin with the same buffer solution in which the hyaluronidase fraction obtained in step b) was diluted and loading the sample, washing with the same buffer solution (about 20 bed volumes) is carried out, after which bound proteins elution is then performed, by progressively increasing the eluent pH. Typically, for the HiTrap® SP FF resin, dilution, column equilibration and washing are carried out with 20 mM sodium phosphate buffer solution at pH 4, while elution is carried out with 50 mM sodium phosphate buffer at pH 4.8; the fractions with high hyaluronidase activity are pooled in a single fraction, which is subjected to strong anion-exchange chromatography [step d)]. Usually, before chromatography, such fraction is diluted 8-12 fold, preferably 10 fold, in a proper equilibration buffer, which allows hyaluronidase to bind to the chosen resin. The resin for step d) is a strong anion-exchange resin comprising quaternary ammonium groups; preferably, a Resource Q® column is used. After loading the sample, washing with the same equilibration buffer is performed and bound proteins elution is then performed by progressively decreasing the pH by 0.5 units, to pH 4. When a Resource Q® column is used, hyaluronidase fraction dilution, column equilibration and washing after sample loading are carried out with 20 mM sodium acetate at pH 5.5; by progressively decreasing the pH as defined above, a first fraction of proteins at pH 5 and two fractions of proteins at pH 4 are obtained; the second fraction eluted at pH 4 has absorbance at 280 nm and enzyme activity higher than the other two fractions, as FIG. 2 shows. By subjecting such fraction to 12% SDS-PAGE chromatography and silver staining (FIG. 6), a single protein band with apparent molecular weight of about 25 kDa is observed. Particularly, 99% of hyaluronidase purified by the above described process has apparent molecular weight of about 25 kDa. Such protein only comprises about 5% of the hyaluronidase present in the supernatant obtained upon fermentation; hence, the process allows obtaining about 20-fold enrichment with about 30% yield.

With respect to other hyaluronidases known to date, that of the invention is highly stable in aqueous solution, is not sensitive towards the action of proteolytic enzymes and has HPLC purity higher than 98% (FIGS. 5a-5h), which is required for therapeutic use; hence, it may be used, alone or in combination with other active ingredients, in the preparation of pharmaceutical or veterinary compositions for the treatment of diseases in which it is necessary or advantageous to degrade the hyaluronic acid present in the organ or tissue affected by the disease.

Thanks to high stability in aqueous solution, the hyaluronidase of the invention can also be formulated in the form of aqueous based compositions, such as solutions, hydrophilic creams, hydrogels, in addition to the form of lipophilic products such as ointments or oily creams.

With regard to human use, the hyaluronidase of the invention can be used for preparation of pharmaceutical compositions for the treatment of edema, particularly traumatic edema, or inflammatory states, such as the hemorrhoidal syndrome; furthermore, it can be used for the preparation of compositions for the treatment of chilblains. The hyaluronidase of the invention can also be used in combination with other drugs whose bioavailability increase is necessary or advantageous.

For example, for the treatment of traumatic edema, combinations of the hyaluronidase according to the invention with anticoagulant and/or fibrinolytic agents are particularly advantageous. Such combinations may also optionally contain one or more steroidal or nonsteroidal anti-inflammatory agents. Furthermore, sulfated hyaluronic acid, which is also known to have antithrombotic and anticoagulant properties, in addition to anti-inflammatory properties, may advantageously be combined with these compositions. An example of sulfated hyaluronic acid that can be used to that end is disclosed, for example, in EP 0702699.

Combinations of the hyaluronidase according to the invention with other active ingredients are also advantageous in the case of injectable preparations containing particularly high molecular weight active ingredients, for example monoclonal antibodies, cytokines or enzymes, which are usually administered intravenously; hyaluronidase allows administering them subcutaneously, according to the so-called EASI (Enzymatically-Augmented Subcutaneous Infusion) procedure, which is mainly employed for fluid replacement in terminal patients, in such a way to limit or avoid nursing care. The hyaluronidase according to the invention can also be employed for the preparation of pharmaceutical compositions for the treatment of resistant solid tumors; in fact, by degrading hyaluronic acid, it lowers the interstitial fluid pressure in the tumor mass, retarding or inhibiting its growth. For the same reason, it also increases the effectiveness of antitumoral active ingredients optionally combined therewith. Hence, a further aspect of the invention relates to pharmaceutical compositions containing hyaluronidase in combination with one or more antitumoral active ingredients, such as vinca alkaloids (vinblastine, vincristine, vinorelbine) and taxanes (paclitaxel).

A further therapeutic use of the hyaluronidase according to the invention relates to the treatment of IgE-mediated allergic forms via enzyme potentiated desensitization (EPD=Enzyme Potentiated Desensitization), which consists of administering extremely low doses of allergens to desensitize subjects susceptible thereto. By associating hyaluronidase with an allergen it is possible to increase the treatment effectiveness, since the allergen more readily reaches the site of action. Hence, a further object of the invention consists of pharmaceutical compositions containing hyaluronidase in association with one or more allergens that induce IgE-mediated allergic reactions. Hyaluronidase also finds use as a diffusion factor of drugs for odontological use in the treatment of oral cavity diseases, for example local anaesthetics and antibiotics; hence, according to a further aspect, the invention relates to pharmaceutical compositions containing the hyaluronidase according to the invention in association with one or more local anaesthetics or antibiotics.

In ophthalmology, hyaluronidase allows to markedly expedite the treatment of spontaneous vitreous haemorrhages and can be used, alone or in combination with other active ingredients, in the preparation of pharmaceutical forms for ophthalmic use, such as solutions, suspensions, gels, creams and ointments, for the treatment of said haemorrhages.

With regard to veterinary use instead, a disease that can effectively be treated with the hyaluronidase of the invention is bovine mastitis; in that case, hyaluronidase can be administered in combination with antibiotics, such as penicillin G, I-IV generation cephalosporins and potentiated aminopenicillins.

Pharmaceutical compositions can be prepared by techniques and excipients known to the skilled person, for example according to what is described in Remington, "The Science and the Practice of Pharmacy", 21$^{st}$ ed. (Lippincott, Williams & Wilkins); such compositions include, particularly, injectable preparations and topical preparations for dermal, transdermal and ophthalmic application. Particularly, topical preparations for epidermal application can be selected from creams, gels, ointments and spray solutions, while topical preparations for ophthalmic application can be selected from creams, gels, ointments solutions and suspensions. As previously noted, thanks to its stability in aqueous solution, the hyaluronidase according to the invention can be formulated in aqueous based products; the choice between an aqueous and oily based formulation can be made by a skilled technician based on common knowledge in the field of pharmaceutical technology, depending on the other components present in the composition.

Finally, the hyaluronidase according to the invention can be used as a reagent in biochemical assays for the qualiquantitative determination of hyaluronic acid.

DESCRIPTION OF THE FIGURES

FIG. 9: comparison between the enzyme activities of some commercially available hyaluronidases and the hyaluronidase according to the invention.

EXPERIMENTAL PART

Figure 1:
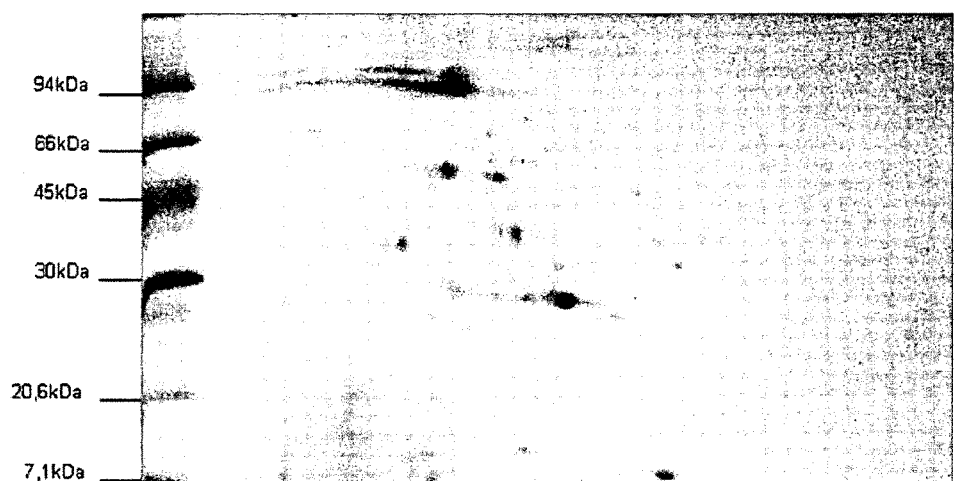
FIG. 1: 2D electrophoresis of the CM-cellulose fraction positive for hyaluronidase activity deriving from culture supernatant of *Streptomyces koganeiensis* ATCC 31394.
Figure 1:
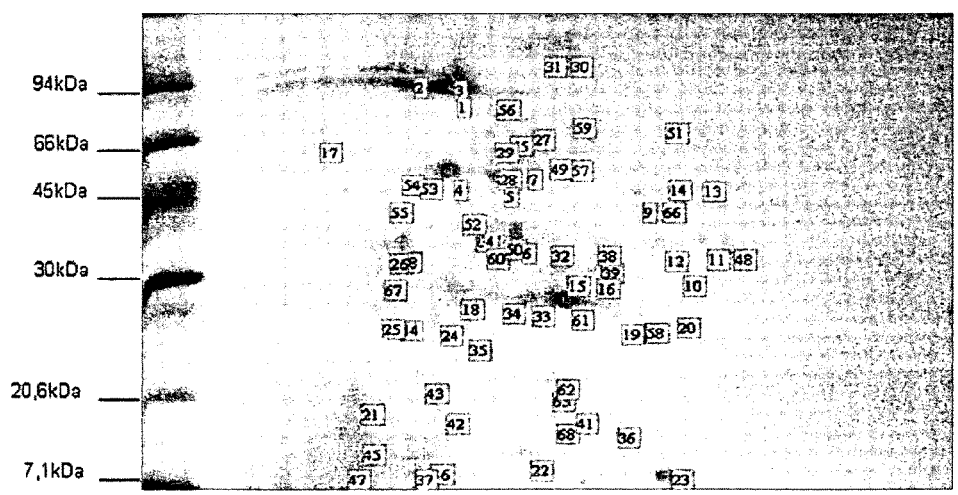
Figure 2:
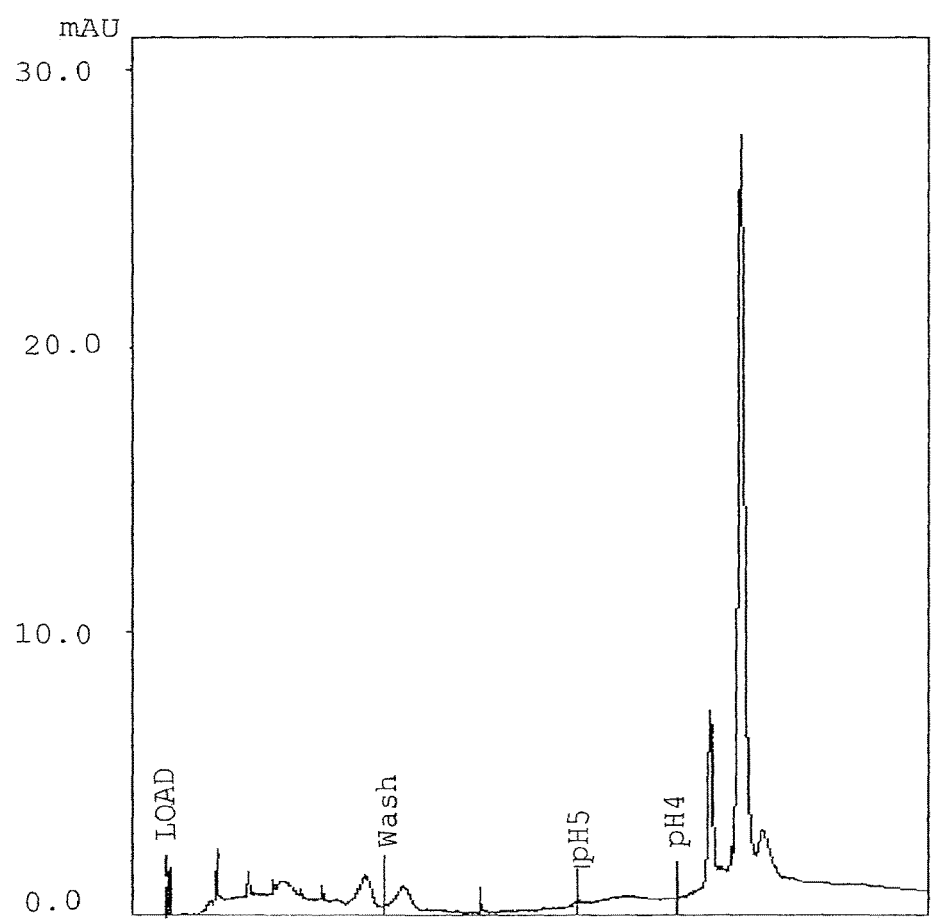
FIG. 2: chromatogram of *Streptomyces koganeiensis* hyaluronidase obtained upon Resource Q® column chromatography (step d).

The invention will now be disclosed in greater detail in the following experimental part, which illustrates the best mode of carrying out the invention, which is not to be intended in a limiting sense.
Materials and Methods
Culture of the Microorganism

*S. koganeiensis* was obtained from American Type Culture Collection (ATCC 31394) and cultured as described in [2]. Briefly, the microorganism was grown in 1 liter of culture medium [(20 g/l yeast extract (Organotechnie) and 5 g/l soy peptone (Solabia), pH 6.9)] at 30° C., shaking at 150 rpm and for about 16 h. Upon growth, the culture was used to inoculate a 50 liter fermentor (Biostat U, B.BRAUN) containing 30 liters of appropriate medium [(10 g/l yeast extract (Organotechnie), 5 g/l soy peptone (Solabia), 3 g/l malt extract (Costantino), 3 g/l dextrin type I (Sigma), 0.2 g/l antifoam (Sigma)]. Before inoculation, the pH was brought to 7.0 with NaOH; during fermentation the pH was monitored, but not controlled, and the temperature was kept at 30° C. throughout fermentation, while shaking was kept at 300 rpm, with aeration of 1.6 VVM (volume of air per volume of culture medium per minute). The fermentation lasted 48 h, a time that corresponded to the highest production of hyaluronidase enzyme activity ($1\times10^5$-$1.3\times10^5$ I.U./l) in the culture supernatant.

At the end of the fermentation the culture was centrifuged at 5000 rpm for 30 min at 4° C. (SORVALL Evolution RC) and filtered with 0.2 μm polyethersulfone tangential flow filters, in such a way to eliminate the *Streptomyces koganeiensis* biomass (which occurred in the form of 1-4 mm diameter roundish hyphal aggregates) and obtain a clarified supernatant containing hyaluronidase.
Determination of Hyaluronidase Activity Hyaluronidase activity was measured by the modified method of Dorfman [3]. Briefly, the product obtained from DEAE- and CM-cellulose chromatographies was diluted in 0.03 M phosphate buffer, 0.82% NaCl, pH 6.3 and 1 ml of the solution thus obtained was mixed with 1 ml of substrate buffer (0.03 M phosphate buffer, 0.82% NaCl, pH 6.3) containing 0.5 mg hyaluronic acid. Enzymatic digestion was carried out at 37° C. for 30 min and at the end of the incubation process turbidity was generated by adding 4 ml of horse serum based acid solution (SIGMA). The optical density at 640 nm was measured exactly 30 min after adding the horse serum based acid solution. A standard of mammalian testicle hyaluronidase (EDQM, FIP Hyaluronidase, H1115000) containing 328 I.U./mg was used to construct a standard curve and the sample activity (in units) was calculated using this curve.
Chromatographies The chromatography resins and columns were purchased from GE Healthcare Life Sciences and kept according to the specifications provided by the supplier. The equilibration and elution stages were carried out with a Fast Performance Liquid Chromatography system (FPLC; AKTA explorer 100, GE Healthcare) at a flow of 40-50 ml/min for the first chromatography and 5 ml/min for the following chromatographies. At the end of each chromatography step the hyaluronidase activity was verified with the modified assay of Dorfman described in the previous step.

For purity analyses by gel filtration the LC-10AD HPLC instrument (SHIMADZU) with a Bio-Sil SEC column (BIO-RAD) was used, eluting with 0.05 M $NaH_2PO_4$, 0.05 M $Na_2HPO_4$, 0.15 M NaCl, pH 6.6, at 1 ml/min. The absorption wavelength used was 214 nm (SPD-10A, SHIMADZU). The protein purity was determined using the LC solution 1.21 SP1 software.
SDS-PAGE Electrophoresis Polyacrylamide gel electrophoresis analyses in the presence of sodium dodecyl sulfate (SDS-PAGE) were carried out using the method of Laemmli [4] on 12% polyacrylamide gel, using a Mini-PROTEAN 3 (BIO-RAD) according to the supplier's instructions. The molecular weight of the purified protein was estimated by comparison with low molecular weight standard proteins (BIO-RAD).
Bidimensional Electrophoresis and Isoelectric Focusing The protein fraction to be analyzed was mixed in proper loading buffer and loaded on pH 3-10 IPG strips (ReadyStrips 7 cm, BIO-RAD); the strip was incubated at 25° C. until sample absorption and loaded on the PROTEAN IEF Cell (BIO-RAD) for isoelectric focusing (IEF).

At the end of the isoelectric focusing run (first dimension) the strip was equilibrated in proper loading and running buffer, then it was loaded in the second dimension on 12% SDS-PAGE, using Mini-PROTEAN 3 cells (BIO-RAD).

Densitometric Analyses

Polyacrylamide gels properly stained with Silver Stain Plus (BIO-RAD) or Coomassie (BIO-RAD), were acquired with a laboratory imager ImageQuant 300 TL (GE Healthcare), while (quantitative and qualitative) analyses were carried out employing the ImageQuant TL image analysis software (GE Healthcare). Image analyses on 2D SDS-PAGE polyacrylamide gels were instead carried out employing the ImageMaster 2D Platinum 6.0 software (GE Healthcare).

Mass Spectrometry

Mass spectrometry analyses for molecular weight determination were carried out using the Ultraflex III TOF/TOF mass spectrometer (BRUKER) and Bruker Protein Mix 1 markers, while protein identification was carried out using the peptide accurate mass values determined by MALDI-MS Voyager DE-PRO system (Applied Biosystems).

Sequencing of the N-Terminal End

N-Terminal amino acid sequencing was carried out according to the Edman degradation method using a pulsed liquid-phase automated protein sequencer (ABI-Perkin Elmer Mod. 477A). The BLAST software [5] was used to carry out homology searches on the GenBank data bank and that of the genome project of web-available *Streptomyces* species.

Comparison Between the Enzyme Activities of Different Types of Hyaluronidases

The enzymatic potential of the hyaluronidase according to the invention was evaluated by comparison with the enzyme activities of some of the most used commercially available hyaluronidases (FIP hyaluronidase standard, bovine testicle hyaluronidase type I-S (SIGMA), bovine testicle hyaluronidase type VI-S (SIGMA), sheep testicle hyaluronidase of type V (SIGMA), *Streptomyces hyalurolyticus* hyaluronidase (SIGMA)), using the above described enzyme assay and the activity value was plotted in FIG. 9 as I.U./mg (protein concentration was determined by BCA Protein Assay Reagent Kit, PIERCE).

Example 1 (Reference Example)—Obtainment, Purification and Characterization of *Streptomyces Koganeiensis* Hyaluronidase According to U.S. Pat. No. 4,258,134

*S. koganeiensis* 31394 ATCC was cultured as described in Materials and Methods; the supernatant obtained from centrifugation, properly filtered with tangential flow filters, was subjected to weak anion-exchange chromatography on DEAE-cellulose. Briefly, 1.2 kg of DEAE-cellulose was equilibrated with 25 mM sodium phosphate buffer at pH 7.0 and packed, then the supernatant, clarified in the same buffer, was loaded on the column and eluted with 25 mM sodium phosphate buffer at pH 7.0 containing 250 mM NaCl; after chromatography, the fraction having hyaluronidase activity was collected and concentrated by ultrafiltration, dialysed with 10 volumes of acetate buffer (pH 5.0) and run through weak cation-exchange chromatography using a CM-cellulose column. Elution was performed by 0.005-0.1 M acetate buffer elution gradient. The positive fraction for hyaluronidase activity was collected upon chromatography, concentrated by ultrafiltration and dialysed with 10 volumes of distilled water (MilliQ, Millipore). The product thus obtained was filtered on 0.2 μm polyethersulfone filters and subjected to assay for determination of hyaluronidase activity, SDS-PAGE, bidimensional electrophoresis and densitometric analysis.

With regard to bidimensional electrophoresis, whose result is reported in FIG. 1, a 600 μl aliquot of the fraction with hyaluronidase activity obtained from chromatography was concentrated to a volume of about 20 μl (about 864 U of hyaluronidase) using BIOMAX 5 k columns (Millipore). The concentrated aliquot was mixed with 125 μl of loading buffer (8 M urea, 2% CHAPS, 50 mM dithiothreitol (DTT), 0.2% (w/v) Bio-Lyte 2/10 ampholyte and bromophenol blue) and loaded on pH 3-10 IPG strips (ReadyStrips 7 cm, BIO-RAD), incubating the sample on the strip at 25° C. for 11 h. After 11 h of sample absorption, the strip was loaded on the PROTEAN IEF Cell (BIO-RAD) for isoelectric focusing (IEF).

At the end of the isoelectric focusing run (first dimension) the strip was first equilibrated for 15 min with a first buffer [(6 M urea, 2% SDS, 0.375 M Tris-HCl (pH 8.8), 20% glycerol, and 2% (w/v) DTT], then with a second buffer [6 M urea, 2% SDS, 0.375 M Tris-HCl (pH 8.8), 20% glycerol]. After equilibration, the strip was loaded in the second dimension on 12% SOS-PAGE, using Mini-PROTEAN 3 cells (BIO-RAD). After the electrophoresis run, the gel was stained with Coomassie PhasLGel Blue R and analyzed, after scanning, by imaging software as described in materials and methods (FIG. 1).

Example 2—Obtainment, Purification and Characterization of the *Streptomyces Koganeiensis* Hyaluronidase According to the Invention 2a) Obtainment and Purification Sample Preparation The clarified supernatant (about 30 liters), obtained from fermentation of *Streptomyces koganeiensis* ATCC 31394, as described in Materials and Methods, was concentrated 10 fold by ultrafiltration through 10-kDa cut-off polyethersulfone filters and its hyaluronidase activity was measured. The concentrated supernatant was then dialysed (10 volumes) with 50 mM sodium acetate solution at pH 4.0 and subjected to step a).

Step a) Weak Cation-Exchange Chromatography

The concentrated and dialysed supernatant was loaded on 200 ml of CM-Sepharose® Fast Flow resin (GE Healthcare), packed in a XK-50 column (GE Healthcare) and equilibrated with 10 bed volumes (bed volumes, BV) of 50 mM sodium acetate buffer at pH 4.0.

After loading, the column was washed with 3 BV of the same buffer, then bound proteins were eluted with 3 BV of 50 mM sodium acetate buffer solution at pH 4.5. Eluted proteins were collected in a single fraction having volume of about 200 ml and subjected to hyaluronidase activity assay.

Step b) Diafiltration and Strong Anion-Exchange Chromatography

The enzymatically active fraction obtained in step a) was subjected to diafiltration for 10 times with 50 mM Tris-HCl, pH 8, equilibration buffer, after which it was loaded on a HiTrap® Q XL column (5 ml), previously equilibrated with 20 BV of the same buffer. After loading the sample, washing with 20 BV of buffer was carried out, then bound proteins were first eluted with 12 BV of 50 mM Tris-HCl buffer, 35 mM NaCl at pH 8 to remove impurities comprised of inactive proteins, after which the enzymatically active fraction was eluted with 14 BV of 50 mM Tris-HCl buffer, 200 mM NaCl at pH 8 and collected in a final volume of about 50 ml. Equilibration, washing and elution were carried out at 5 ml/min flow.

Step c) Strong Cation-Exchange Chromatography

The fraction deriving from step b) was diluted 10 fold with 20 mM sodium acetate buffer at pH 4 and loaded on HiTrap® SP FF column, previously equilibrated with 20 BV of the same solution. After a first washing with 20 BV of the same solution, bound proteins were eluted with 10 BV of 50 mM sodium phosphate buffer at pH 4. Eluted proteins were collected in a fraction having a volume of about 45 ml and subjected to hyaluronidase enzyme activity assay. Equilibration, washing and elution were carried out at 5 ml/min flow.

Step d) Strong Anion-Exchange Chromatography

The enzymatically active fraction obtained in step c) was diluted 10 fold in 20 mM sodium acetate buffer at pH 5.5 and loaded on a Resource Q® column, previously equilibrated with 20 BV of the same buffer. After loading the sample, washing with 20 BV of the same buffer was carried out, then pH was lowered to 5 and elution with 10 BV of solution was carried out in such a way to remove the impurities comprised of inactive proteins. The pH was then further lowered to 4 and elution with 15 BV of buffer was carried out. The second peak eluted at this pH value, having higher absorbance, was collected in a final volume of about 10-15 ml and subjected to ultrafiltration and dialysis with 10 volumes of MilliQ water (Millipore). Equilibration, washing and elution were carried out at 5 ml/min flow.

Figure 3:
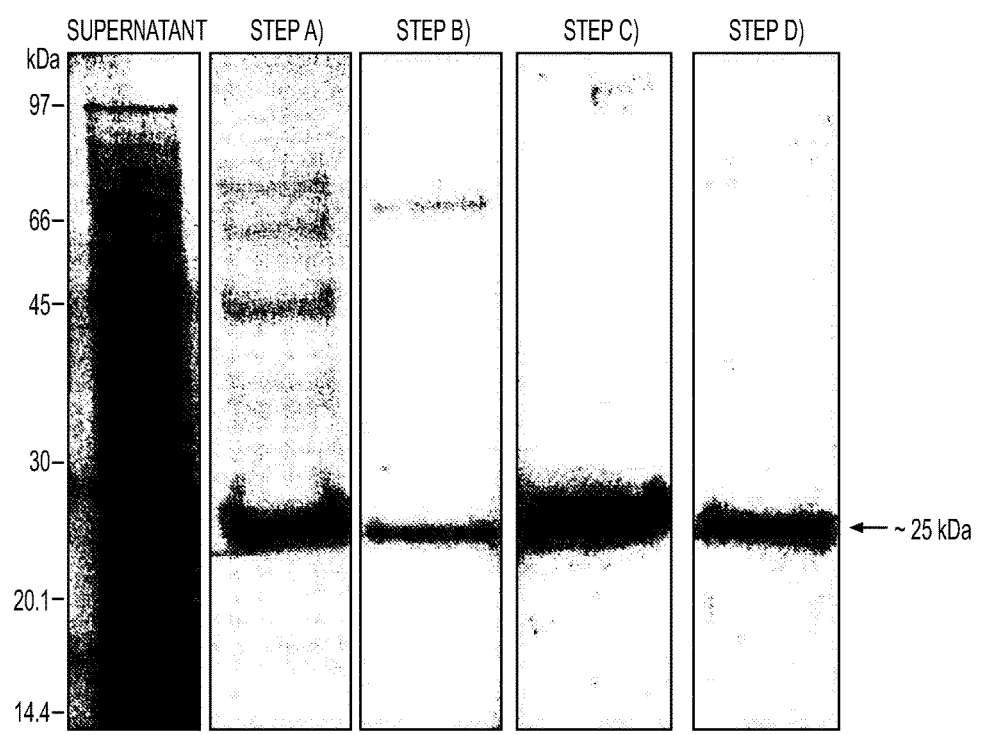
FIG. 3: 12% SDS-PAGE protein pattern of the fractions obtained at the end of each purification step according to the invention compared to the supernatant protein pattern.

All of the eluted protein fractions, either enzymatically active or inactive or little active, were then analyzed by 12% SDS-PAGE as described in Materials and Methods and then stained with silver stain according to the instructions provided by the supplier; in all of the fractions with the highest hyaluronidase activity a more marked protein band at about 25 kDa was present (FIG. 3).

2b) Analysis and Characterization

HPLC Analysis by Gel Filtration

Figure 4:
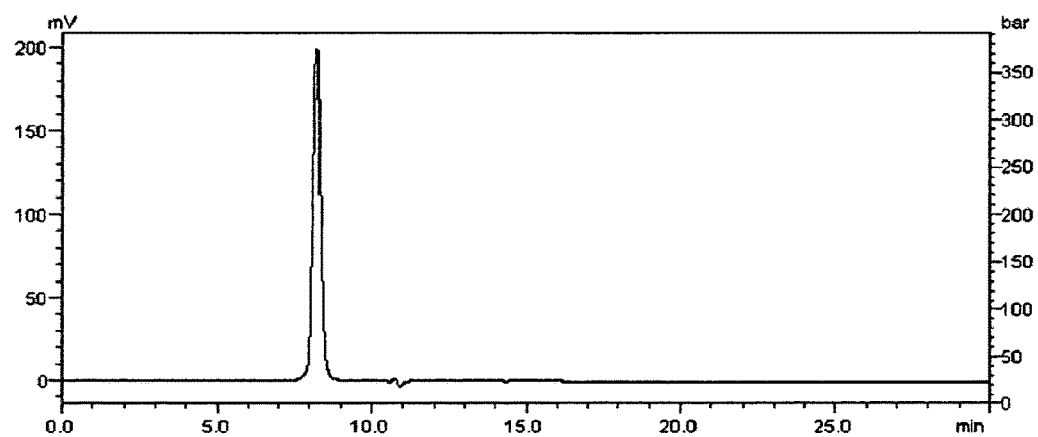
FIG. 4: analysis of hyaluronidase purity by HPLC on Bio-Sil SEC gel filtration column [step d)].
Figure 5A:
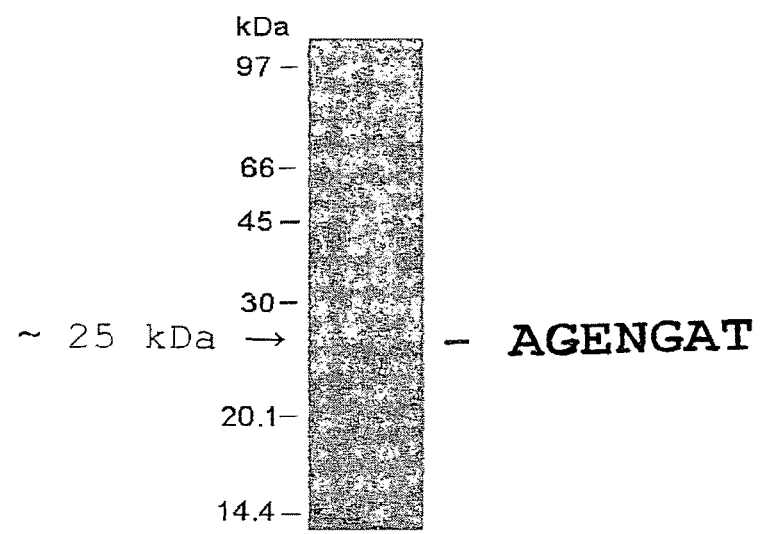
FIGS. 5a-5h: SDS-PAGE analysis and absorption spectra of the N-terminal sequencing of hyaluronidase obtained in step d).
Figure 5B:
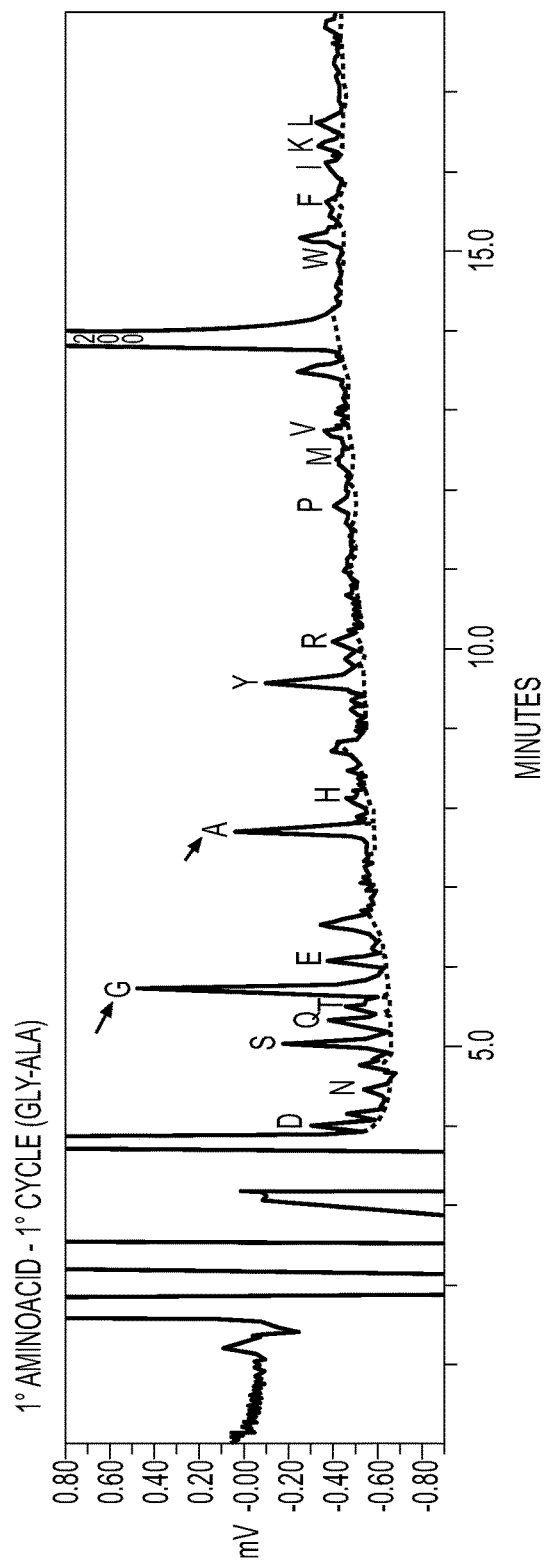
Figure 5C:
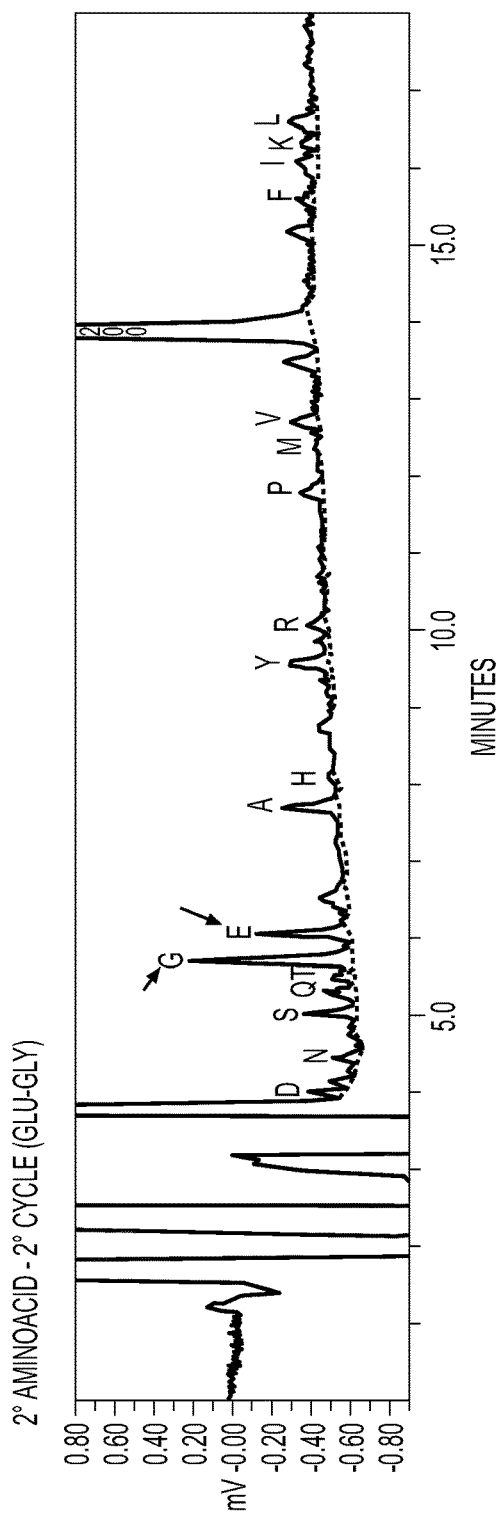
Figure 5D:
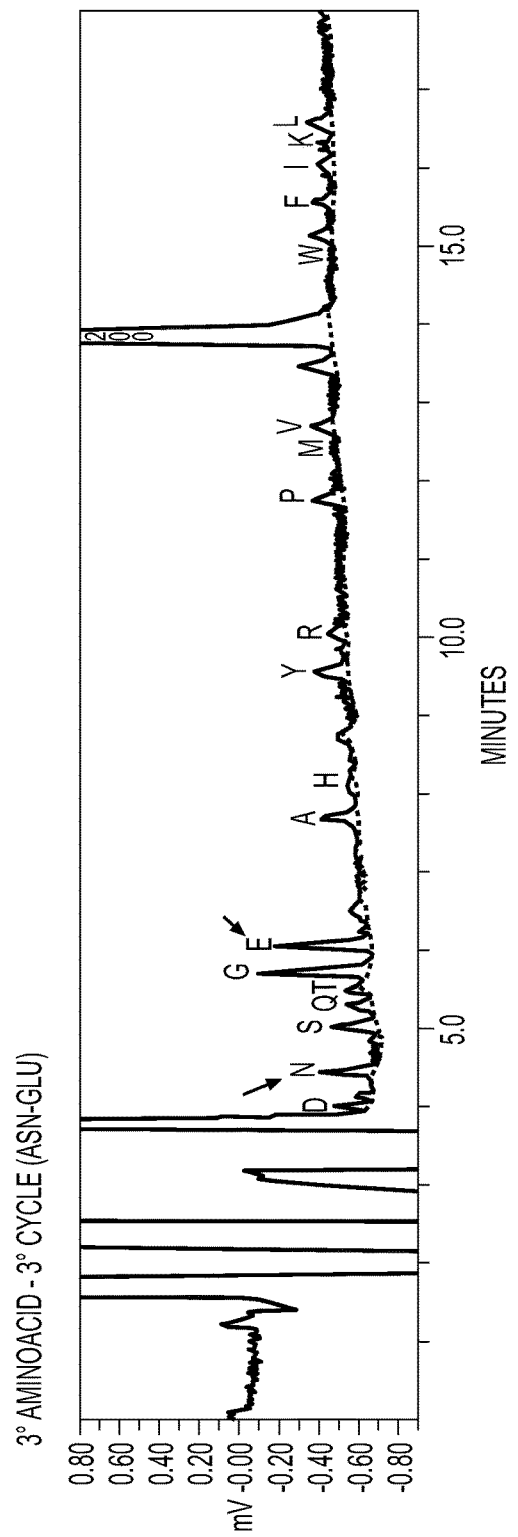
Figure 5E:
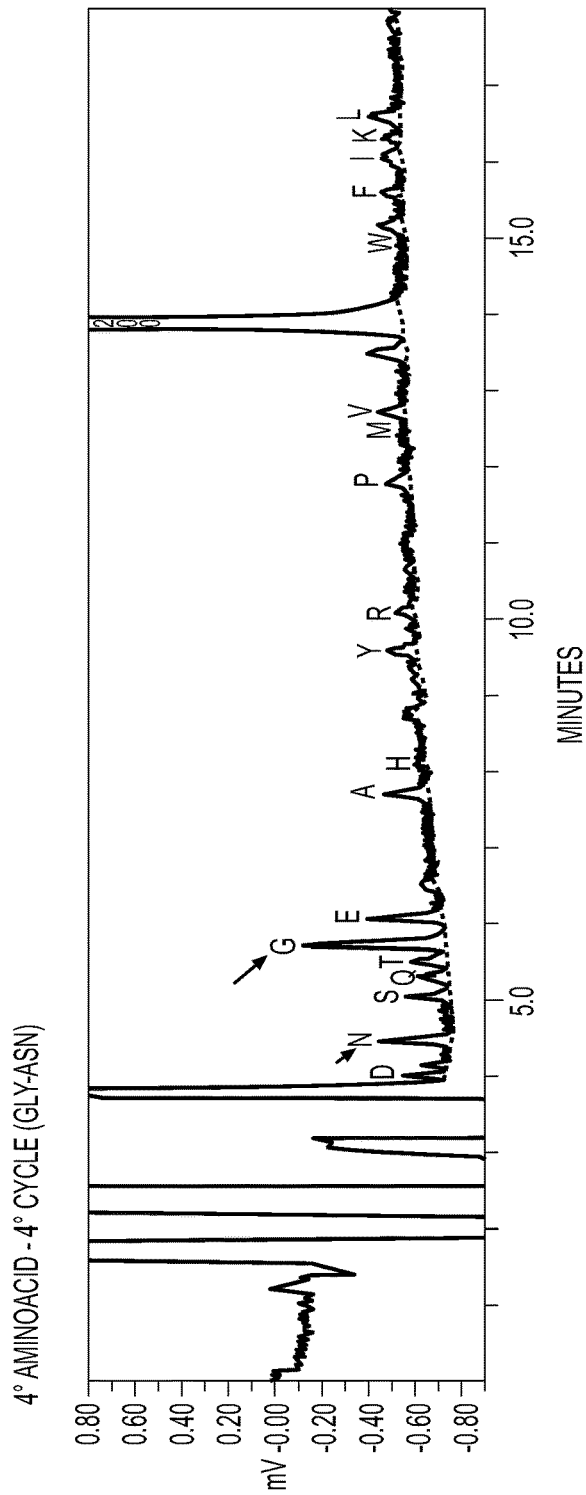
Figure 5F:
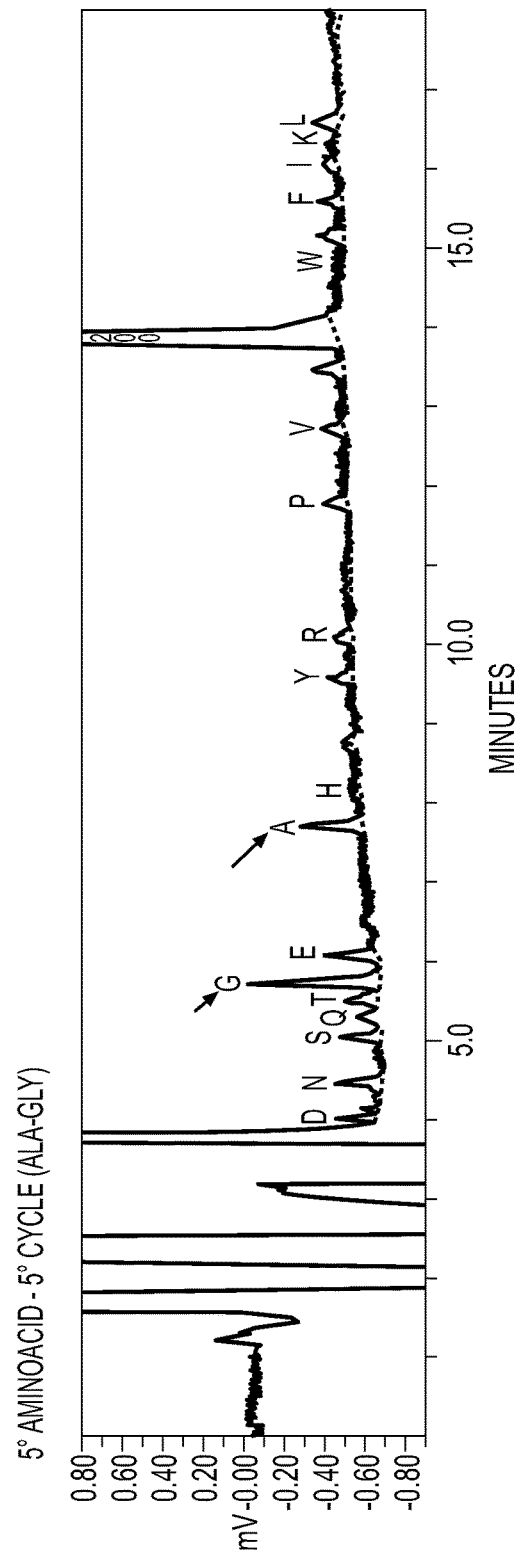
Figure 5G:
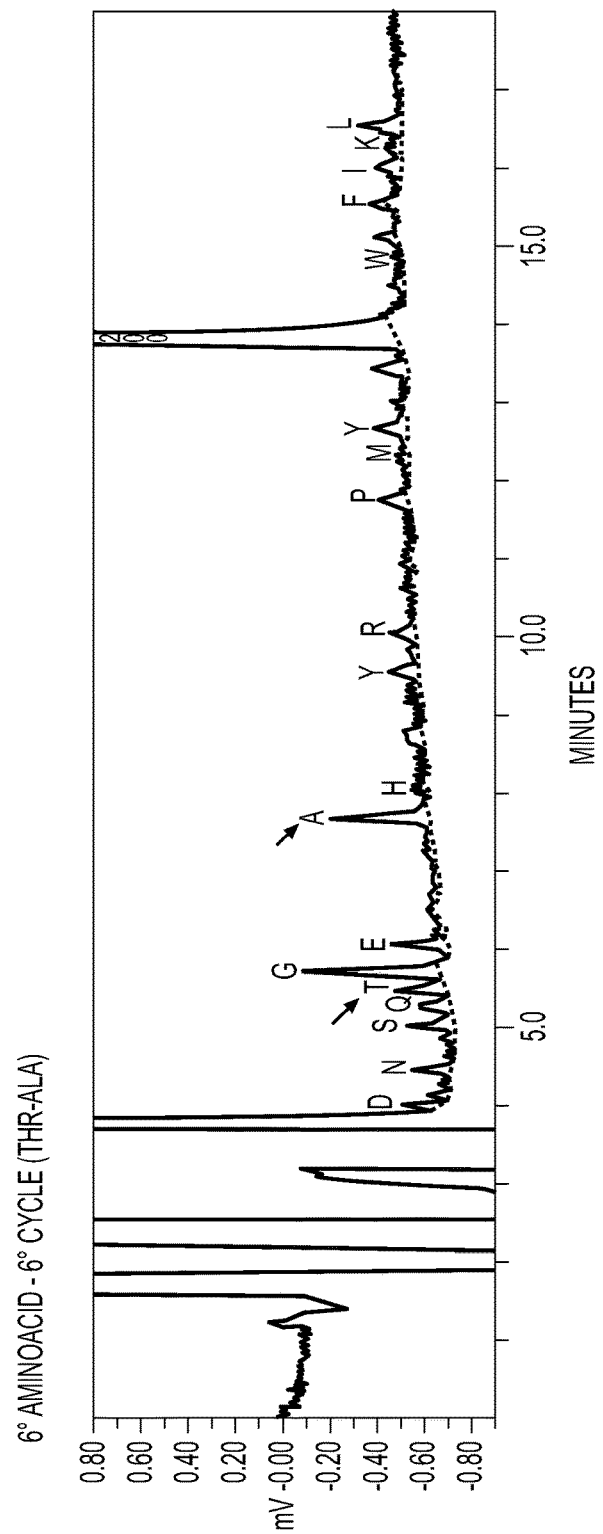
Figure 5H:
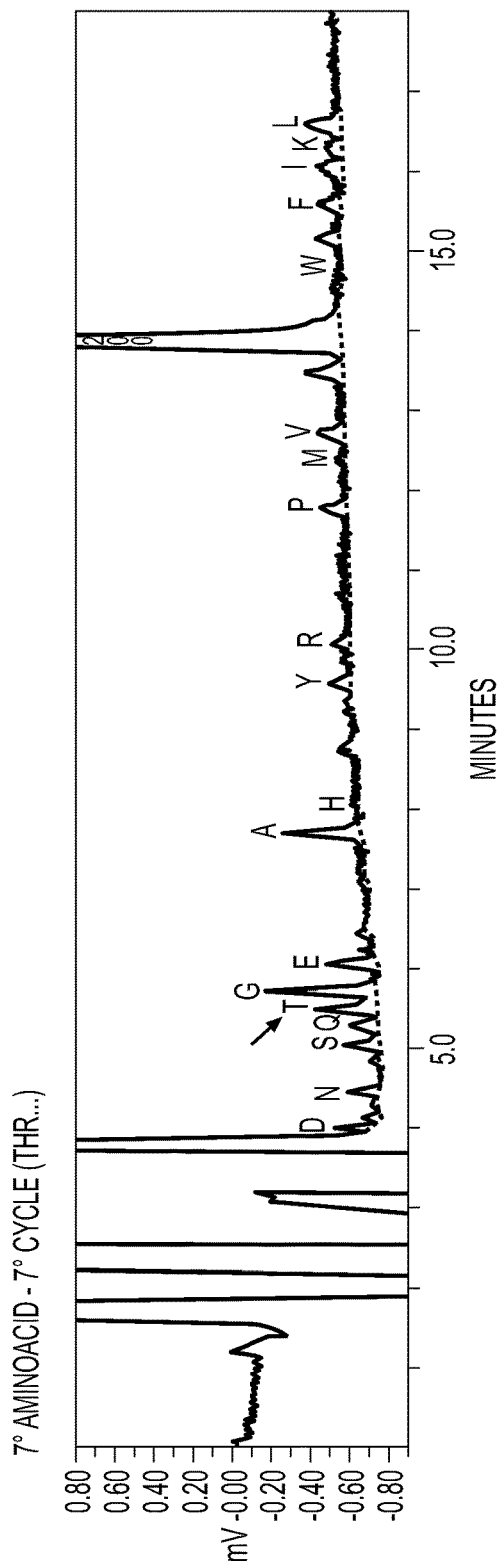

The fraction obtained in step d) was subjected to gel filtration column HPLC as described in Materials and Methods. The result of the analysis is reported in FIG. 4.

Mass Spectrometry

The fraction obtained in step d) was subjected to 12% SDS-PAGE electrophoresis. At the end of the run the gel was stained with Coomassie Brilliant Blue G-250 (BIO-RAD) and the protein excised from the gel was digested with trypsin (BIO-RAD). A peptide mass pattern was obtained using the MALDI-MS Voyager DE-PRO system (Applied Biosystems). The obtained peptide masses were used for the data bank searches for the protein identification.

N-Terminal Sequencing

The fraction obtained in step d) was subjected to SDS-PAGE electrophoresis on 12% gel, as described above, then blotting to polyvinylidene difluoride membrane (BIO-RAD) and stained according to the instructions provided by the supplier. The band was excised with a scalpel, trying to obtain a piece of the smallest possible size (3 mm×10 mm) and was loaded in the sequencer reaction chamber.

Determination of Hyaluronidase Activity by Non-Denaturing SDS-PAGE

The protein samples to be analyzed for hyaluronidase enzyme activity [hyaluronidase and unbound proteins obtained in step d) and hyaluronidase obtained according to U.S. Pat. No. 4,258,134 chromatography] were separated in duplicate on native 8% polyacrylamide gel impregnated with 0.17 mg/ml of hyaluronic acid. After the electrophoresis run, the gel was washed three times with 0.1 M sodium formate, 0.05 M NaCl, pH 4.0, and incubated overnight in the same solution at 37° C. The gel was washed three times in 3% acetic acid and stained for 2 h at room temperature in 0.5% (w/v) Alcian blue (SIGMA) and 3% acetic acid solution. The gel was then destained in 7% sodium acetate solution for at least 1 h.

Figure 6:
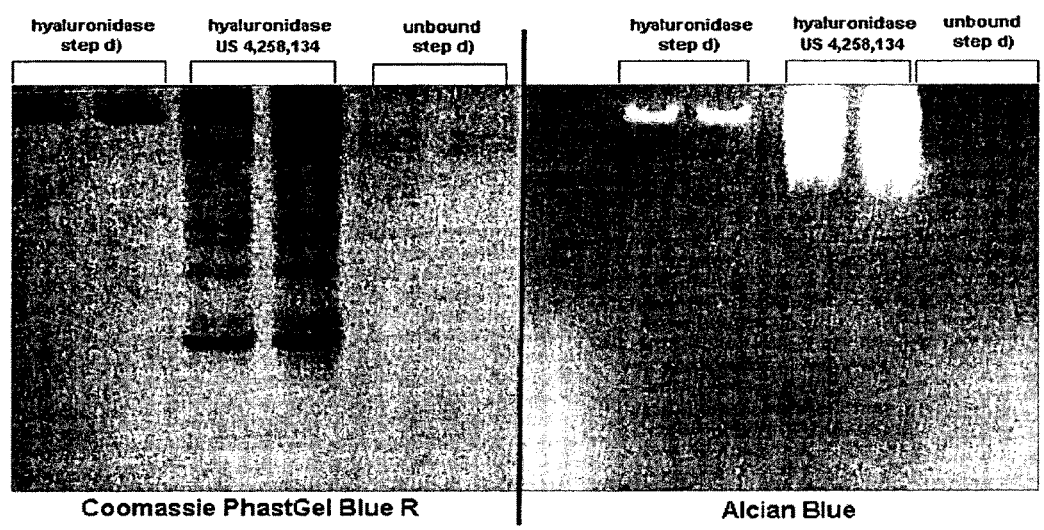
FIG. 6: non-denaturing SDS-PAGE analysis for determination of hyaluronidase activity; comparison between hyaluronidase obtained in step d) and hyaluronidase obtained according to U.S. Pat. No. 4,258,134.

Proteins that exhibited hyaluronidase activity were detected as pale bands on the gel blue background [6]. Native-PAGE prepared in the same way, but stained with Coomassie Brilliant Blue G-250 (BIO-RAD) was used as a control (FIG. 6).

Passive Elution of the Protein from Native Polyacrylamide Gel

The protein band with hyaluronidase activity was excised from the native polyacrylamide gel stained with Coomassie Brilliant Blue G-250 and placed within a 1.5 ml sterile tube. 0.5 ml of elution buffer (50 mM Tris-HCl, 150 mM NaCl, and 0.1 mM EDTA; pH 7.5) was added to the excised piece of gel, in such a way that it was completely immersed. The piece of gel was homogenized with a sterile pestle and incubated in an orbital shaker at 30° C. overnight. After incubation, the homogenized gel was centrifuged at 5,000-10,000×g (5402 centrifuge, eppendorf) for 10 min and the supernatant was very carefully taken out and transferred to a new 1.5 ml tube. After being concentrated 10 fold with BIOMAX 5 k column (Millipore), the supernatant was verified for the presence of the eluted protein by SDS-PAGE, and afterwards it was subjected to hyaluronidase activity assay and, as a confirmation, N-terminal sequencing (FIG. 5).

Determination of the Protein Molecular Weight by Mass Spectrometry

Figure 7:
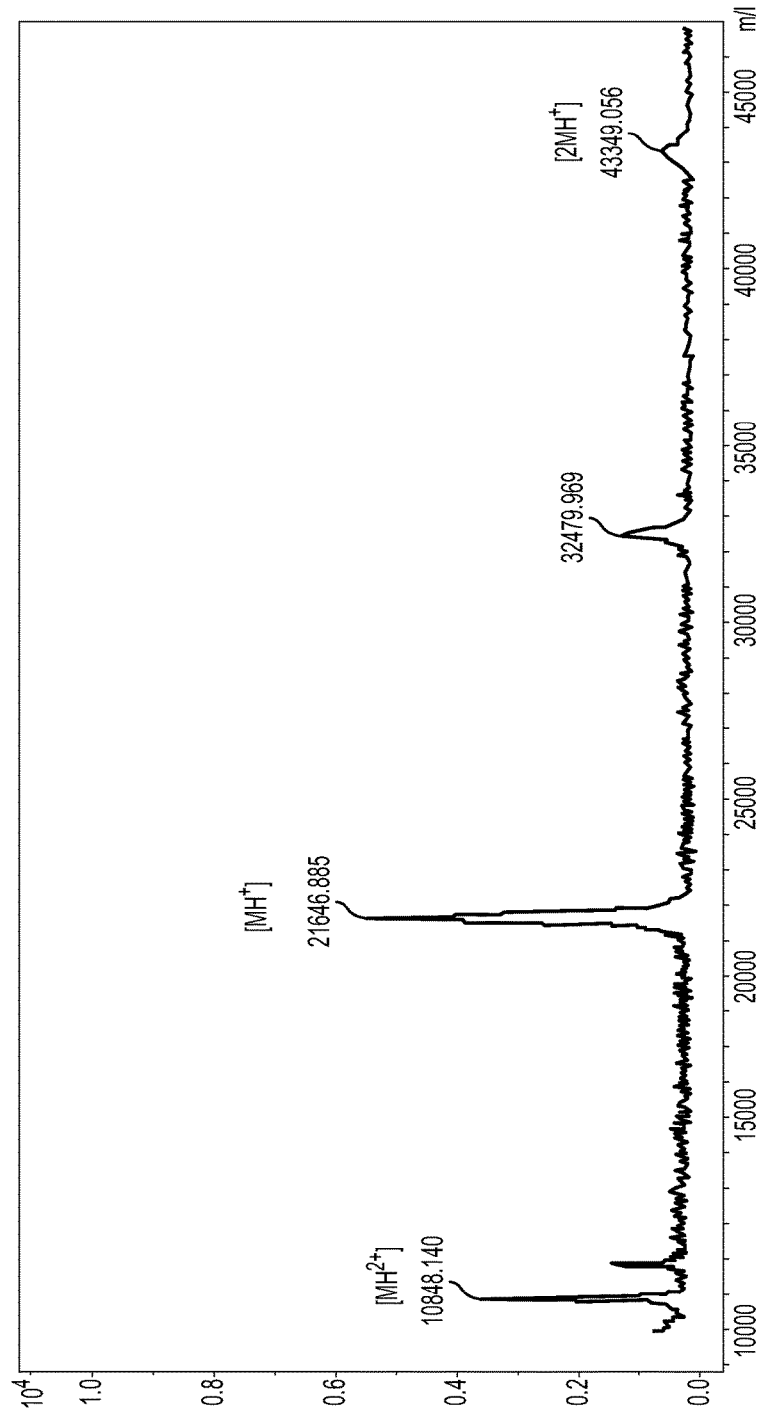
FIG. 7: mass spectrometry determination of the molecular weight of hyaluronidase obtained in step d).

1 µl hyaluronidase (about 0.5 µg) was mixed with 1 µl of a solution comprised of 20 µg/µl sinapinic acid (SA) in 50% acetonitrile with 0.1% trifluoroacetic acid (TFA). The obtained mixture was transferred onto MALDI plate and subjected to analysis as noted in Materials and Methods. The result of the analysis is reported in FIG. 7.

Isoelectric Focusing

Figure 8:
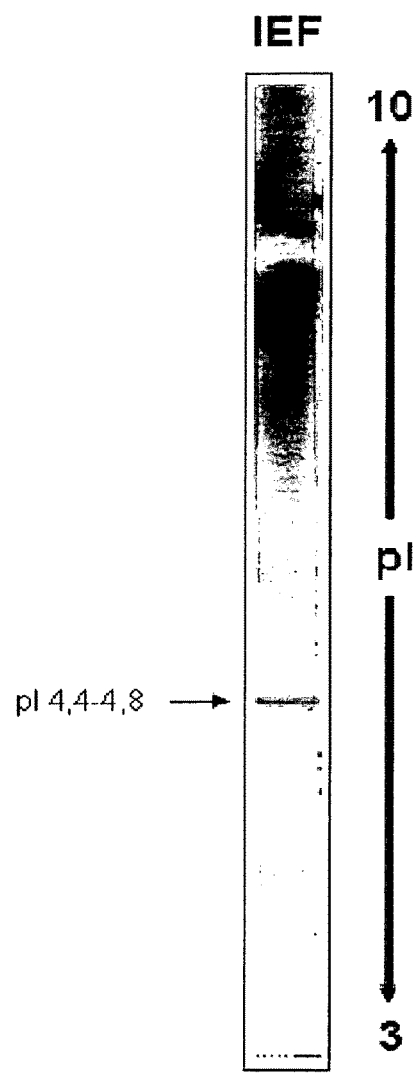
FIG. 8: determination of the isoelectric point of hyaluronidase obtained in step d).

A 20 µl aliquot (20 µg) of hyaluronidase obtained in step d), was mixed with 125 µl of loading buffer [8 M urea, 2% CHAPS, 50 mM dithiothreitol (DTT), 0.2% (w/v) Bio-Lyte 2/10 ampholyte and bromophenol blue] and loaded on pH 3-10 IPG strip (ReadyStrips 7 cm, BIO-RAD), incubating the sample on the strip at 25° C. for 11 h. After 11 h of sample absorption, the strip was loaded for isoelectric focusing (IEF) on the PROTEAN IEF Cell (BIO-RAD). At the end of the isoelectric focusing run, the strip was dried with filter paper (Whatman), moistened with MilliQ water, and stained for 45 min using IEF Gel Staining solution (BIO-RAD). The strip was destained for 1 h or longer with destaining solution (Destain solution, Coomassie R-250, BIO-RAD). The sample isoelectric point was determined by comparison with the reference standards isoelectric points (IEF Marker pH 3-10, SERVA). The result of the analysis is reported in FIG. 8.

Comparison Between the Enzyme Activities of Different Types of Hyaluronidases

The result of this assay demonstrates that the hyaluronidase according to the invention has an activity about three times higher than the most active among those used for the comparison (FIG. 9).

Sequencing

Sequencing of the N-terminal end, which was carried out as described in materials and methods, allowed to establish that it contains the following amino acid sequence:

(SEQ ID NO: 1)
Ala-Gly-Glu-Asn-Gly-Ala-Thr-Thr-Thr-Phe-Asp-Gly-Pro-Val-Ala

Example 3—Pharmaceutical Preparations

| Preparation 1 - Hydrophilic gel | |
|---|---|
| Components | Amounts (I.U. or mg/1 g of hydrogel) |
| Hyaluronidase | 150 I.U. |
| Carbomer 974P | 15 mg |
| Glycerol | 100 mg |
| Propylene glycol | 66.75 mg |
| Triethanolamine (TEA) | 13.25 mg |
| Polyethylene glycol 400 | 66.75 mg |
| Methyl p-hydroxybenzoate | 2 mg |
| Propyl p-hydroxybenzoate | 0.2 mg |
| Purified water | q.s. to 1 g |

Methyl- and propyl-paraben were dissolved in purified water at 80° C. After the solution cooled down to room temperature, hyaluronidase was added, shaking until completely dissolved, after which PEG 400 was added, continuing to shake until dissolved. To this solution Carbomer® 974P was added, continuing to shake until homogeneous dispersion and complete hydration thereof, then TEA was added to obtain the aqueous phase gelation. Finally, always under shaking, glycerol and propylene glycol were added.

| Preparation 2 - Hydrophilic cream (o/w emulsion) | |
|---|---|
| Components | Amounts (I.U. or mg/1 g of cream) |
| Hyaluronidase | 150 I.U. |
| Tefose 1500 | 110 mg |
| Glycerol | 80 mg |
| Stearic acid | 33 mg |
| Liquid paraffin | 40 mg |
| Methyl p-hydroxybenzoate | 1 mg |
| Purified water | q.s. to 1 g |

For the preparation of the oily phase, liquid paraffin, stearic acid and Tefose® 1500 were melted under shaking at 50° C. Separately, the aqueous phase was prepared by initial solution of methyl-paraben at 80° C., subsequent cooling to room temperature and incorporation of glycerol and hyaluronidase under shaking until completely dissolved.

The aqueous phase was added to the oily phase, proceeding with emulsification, after which the obtained o/w emulsion was cooled under shaking to room temperature.

| Preparation 3 - Ointment | |
|---|---|
| Components | Amounts (I.U. or mg/1 g of ointment) |
| Hyaluronidase | 150 I.U. |
| Light liquid paraffin | 200 mg |
| White vaseline | q.s. to 1 g |

The ointment base was prepared by melting light liquid paraffin and white vaseline under shaking at 70° C. After cooling to room temperature, hyaluronidase was incorporated, mixing until obtaining a homogeneous suspension.

| Preparation 4 - Lipogel | |
|---|---|
| Components | Amounts (I.U. or mg/1 g of lipogel) |
| Hyaluronidase | 150 I.U. |
| Hydrogenated castor oil | 10 mg |
| Cetostearyl alcohol | 50 mg |
| White vaseline | 365 mg |
| Light liquid paraffin | q.s. to 1 g |

Light liquid paraffin, white vaseline and the cetylstearyl alcohol were melted under shaking at 90° C., after which, under shaking, hydrogenated castor oil (lipogelation agent) was added until homogeneous solution. After slowly cooling to room temperature, hyaluronidase was incorporated, mixing until obtaining a homogeneous suspension.

| Preparation 5 - Injectable solutions for intramuscular or subcutaneous use | |
|---|---|
| Components | Amounts (I.U. or mg/ml of sol.) |
| Hyaluronidase | 200 I.U. |
| Lactose | 0.93 |
| Potassium Phosphate Dibasic | 0.36 |
| Potassium Phosphate Monobasic | 0.23 |
| Sodium chloride | 9 |

Lactose and hyaluronidase were dissolved, under shaking, in buffered saline at pH 6.4-7.2, prepared at room temperature and the solution thus obtained was filtered on 0.22-micron filters.

REFERENCES

[1] Mclean, D., Fishbein, M C., Maroko, P R. & AND Braunwald AND. 1976. Science, 194: 99-200.

[2] Yoshida, K., Fujii, T., Kikuchi, H. 1981. U.S. Pat. No. 4,258,134 and European patent EP 0 005 751

[3] Dorfman, A. 1955. Methods in Enzymology, 1: 166-173.

[4] Laemmli, U. K. 1970. Cleavage of structural proteins during the assembly of head of bacteriophage T4. Nature (London) 227: 680-685.

[5] Altschul S F, Madden T L, Schäffer A A, Zhang J, Zhang Z, Miller W, Lipman D J. 1997. Gapped BLAST and PSI-BLAST: a new generation of protein database search programs. Nucleic Acids Res. 25: 3389-3402.

[6] Guntenhoener, M. W., Pogrel, M. A., and Stern, R. 1992. Matrix 12, 388-396.

[7] Lachmann S, Rommeleare J, Nüesch J P. 2003. Novel PKCeta is required to activate replicative functions of the major nonstructural protein NS1 of minute virus of mice. J Virol 2003; 77 (14):8048-60.

The invention claimed is:

1. A process for preparing hyaluronidase from *Streptomyces koganeiensis* ATCC 31394 comprising:
   a) fermenting *Streptomyces koganeiensis* ATCC 31394 and obtaining a supernatant;
   b) submitting the supernatant obtained from the fermentation of *Streptomyces koganeiensis* ATCC 31394 to weak cation-exchange chromatography and isolating a protein fraction with hyaluronidase activity;
   c) submitting the protein fraction with hyaluronidase activity from step b) to diafiltration and strong anion-exchange chromatography and isolating a protein fraction with hyaluronidase activity;
   d) submitting the protein fraction with hyaluronidase activity from step c) to strong cation-exchange chromatography and isolating a protein fraction with hyaluronidase activity;
   e) submitting the protein fraction with hyaluronidase activity from step d) to strong anion-exchange chromatography and isolating a protein fraction with hyaluronidase activity, thereby obtaining hyaluronidase consisting of:
   a) an N-terminal amino acid sequence set forth in SEQ ID NO: 1,
   b) a molecular weight of 21.6 kDa,
   c) an isoelectric point (pI) ranging from 4.4 to 4.8,
   d) a relative enzymatic activity equal to or higher than 40,000 I.U./mg, measured against hyaluronidase BRP from bovine testis EDQM, FIP, Hyaluronidase, H1115000 and
   e) a HPLC purity degree higher than 98%, wherein said hyaluronidase is stable in aqueous solution and not sensitive to the action of proteolytic enzymes.

* * * * *

SEQUENCE LISTING

<160> NUMBER OF SEQ ID NOS: 1

<210> SEQ ID NO 1
<211> LENGTH: 15
<212> TYPE: PRT
<213> ORGANISM: Streptomyces koganeiensis ATCC 31394

<400> SEQUENCE: 1

```
Ala Gly Glu Asn Gly Ala Thr Thr Thr Phe Asp Gly Pro Val Ala
1               5                   10                  15
```